United States Patent [19]

Motegi et al.

[11] Patent Number: 4,902,815
[45] Date of Patent: Feb. 20, 1990

[54] PLANT GROWTH REGULANT

[75] Inventors: Takeo Motegi; Yasuya Sakuraba; Hiroyuki Iguchi; Kaoru Kasahara, all of Tokyo, Japan

[73] Assignee: Hodogaya Chemical Co., Ltd., Tokyo, Japan

[21] Appl. No.: 163,729

[22] Filed: Mar. 3, 1988

[30] Foreign Application Priority Data

Mar. 5, 1987 [JP] Japan ............................. 62-48716

[51] Int. Cl.$^4$ .............................................. C07C 101/72
[52] U.S. Cl. ........................................ 560/45; 562/455
[58] Field of Search ............................ 562/455; 560/45

[56] References Cited

U.S. PATENT DOCUMENTS 3,907,792  9/1975  Mieville .................................. 560/45

OTHER PUBLICATIONS

Fundamentals of Chemical Regulation of Plants Growth and Productivity, by G. S. Muromtsev et al, Moscow, V/O "Agropromizdat", 1987 (English translation).

Primary Examiner—Bruce Gray
Attorney, Agent, or Firm—Oblon, Spivak, McClelland, Maier & Neustadt

[57] ABSTRACT

A plant growth regulant containing a benzamide derivative of the formula:

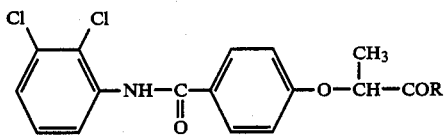

wherein R is hydroxyl, alkoxy, alkoxyalkoxy, alkoxyalkoxyalkoxy, alkenylalkoxy, alkenylalkoxyalkoxy, alkynylalkoxy, alkynylalkoxyalkoxy, monoalkylamino, dialkylamino or O-cat wherein cat is an inorganic or organic cation.

2 Claims, No Drawings

PLANT GROWTH REGULANT

The present invention relates to a control of the growth of plants. More particularly, the present invention relates to a plant growth regulant and use of a certain specific compound as a plant growth regulant.

In the case of rice or wheat, it happens not infrequently that the crop plants are lodged by wind or rain immediately before the harvest time, whereby the yield drops substantially. There have been proposed some chemical compounds which are intended to regulate the stems to be short and strong against such lodging force. However, there have been problems such that an attempt to control the stems to make them sufficiently strong, is likely to adversely affect the panicles, or the effectiveness of such treatment is very much influenced by the weather, the growing state or the timing or season for the treatment.

In the case of a lawn or hedge trees, or grass in a non-agricultural field, even if such plants are neatly trimmed or mown, they tend to grow quickly again. There have been some drugs tested for effectiveness so that cutting or mowning may be thereby omitted. However, a satisfactory compound has not yet been available.

In the case of fruit trees, a thinning agent is frequently used to prevent the fruit trees from bearing so many fruits that the fruits tend to be small in size. However, the range of application is very narrow, and the method for its use is very difficult.

On the other hand, it is also an important area to increase the number of flowers or fruits.

In the case of root-crops, the quality of the root degrades when flower stalk develops. Therefore, a compound to control the development of the flower stalk is desired.

In the case of sugar cane, it has been attempted to increase the yield by preventing the heading or by increasing the sugar content by some physiological action.

Further, in the case of potatoes or onions, it is important to delay the sprout during their storage.

The above instances are merely exemplary, and there may be many other areas where the growth of plants is desired to be controlled. In each area, there may be some compounds which are actually used. However, there has been no compound which is fully satisfactory. It is therefore desired to develop an improved compound.

The present inventors have conducted extensive research on the plant activities and have found that when applied to the foliages of various plants, certain specific compounds exhibit various interesting activities including activities to shorten stems, to promote tillering, to control development of fresh buds or in some cases to promote development of flower buds. On the basis of this discovery, a further study has been made to utilize such activities for a plant growth regulant. As a result, the present invention has been accomplished.

The present invention provides a plant growth regulant containing a benzamide derivative of the formula:

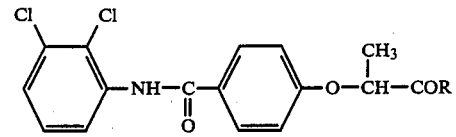

wherein R is hydroxyl, alkoxy, alkoxyalkoxy, alkoxyalkoxyalkoxy, alkenylalkoxy, alkenylalkoxyalkoxy, alkynylalkoxy, alkynylalkoxyalkoxy, monoalkylamino, dialkylamino or O-cat wherein cat is an inorganic or organic cation.

Now, the present invention will be described in detail with reference to the preferred embodiments.

To practice the present invention, the compounds of the present invention may be formulated, depending upon their physical and chemical properties, into any formulations including a formulation to be diluted with water for application, such as a wettable powder, an emulsifiable concentrate, an aqueous solution, a liquid formulation or a flowable and a formulation to be applied as it is, such as a dust or a micro-granule formulation, as the case requires, so long as such formulations are suitable for foliar application.

As a carrier, an inert inorganic substance such as bentonite, clay, zeolite or talc may be used. As an organic solvent, a solvent in which various compounds are well soluble, such as xylene, toluene, cyclohexanone or a glycol may be employed. Further, as a dispersing agent, an emulsifying agent or a fixing agent, there may be employed an anionic or nonionic surface active agent such as lignin sulfonate, naphthalene sulfonate, dialkyl sulfosuccinate, polyoxyethylene nonyl phenyl ether, polyoxyethylene stearyl ether or polyoxyethylene dodecyl ether.

The plant growth regulant of the present invention may be, as the case requires, combined with a fungicide or an insecticide in the form of a unitary formulation or as a tank mix for application.

The dose varies depending upon the type of the plant to be treated, the type of the compound or the time of application. However, in the case of rice plant, the dose of the active ingredient is usually within a range of from 0.5 to 5 g/a (gram/are), preferably from 1 to 2.5 g/a. The application may be conducted in any manner so long as the regulant can be applied uniformly to the foliage. For example, it may be applied by means of a pressure sprayer as diluted with water in an amount of from 2 to 20 liter/a. There is no particular restriction as to the concentration.

In the case of wheat, barley, etc, the difference in the sensitivity due to the growing stage is slightly larger than rice. When used as an agent for reducing the lodging, it is usually necessary to apply the plant growth regulant in an amount more than required for rice. In other respects, the application method is substantially the same as in the case of rice. The dose of the active ingredient is usually within a range of from 1.5 to 15 g/a, preferably from 3 to 10 g/a.

In the case of lawn, the dose of the active ingredient is usually from 1.5 to 15 g/a for grass of the type with its stem growing remarkably such as Bermuda grass, although it may vary depending upon the season for the treatment or the duration of the effective period. For grass of the type where it is required to control the growth of leaves, such as Zoysia, a substantially large amount is required.

In the case of trees, a very long period of effectiveness is required, and the dose of the active ingredient is usually from 10 to 50 g/a. In the case of a non-cropland, the dose of the active ingredient may sometimes exceed 50 g/a in order to affect against large size weeds such as Japanese pampas grass (*Miscanthus sinensis*).

On the other hand, in the area where the effectiveness is required for a relatively short period of time, such as in the case of inducing flower buds or thinning fruits, the dose of the active ingredient may be as small as from 0.1 to 2 g/a.

Now, the present invention will be described in further detail with reference to Test Examples.

In Table 1, representative compounds of the present invention are given. These compounds will be referred to hereinafter by the compound numbers identified in Table 1.

TABLE 1

| Compound No. | Structure |
|---|---|
| 1. | 2,3-Cl$_2$-C$_6$H$_3$-NH-C(=O)-C$_6$H$_4$-O-CH(CH$_3$)-COOH |
| 2. | 2,3-Cl$_2$-C$_6$H$_3$-NH-C(=O)-C$_6$H$_4$-O-CH(CH$_3$)-COOCH$_3$ |
| 3. | 2,3-Cl$_2$-C$_6$H$_3$-NH-C(=O)-C$_6$H$_4$-O-CH(CH$_3$)-COOC$_2$H$_5$ |
| 4. | 2,3-Cl$_2$-C$_6$H$_3$-NH-C(=O)-C$_6$H$_4$-O-CH(CH$_3$)-COOC$_4$H$_9$ |
| 5. | 2,3-Cl$_2$-C$_6$H$_3$-NH-C(=O)-C$_6$H$_4$-O-CH(CH$_3$)-COOC$_{12}$H$_{25}$ |
| 6. | 2,3-Cl$_2$-C$_6$H$_3$-NH-C(=O)-C$_6$H$_4$-O-CH(CH$_3$)-COO-CH$_2$-CH$_2$-O-C$_4$H$_9$-n |
| 7. | 2,3-Cl$_2$-C$_6$H$_3$-NH-C(=O)-C$_6$H$_4$-O-CH(CH$_3$)-COO-(CH$_2$-CH$_2$-O)$_2$-C$_4$H$_9$-n |
| 8. | 2,3-Cl$_2$-C$_6$H$_3$-NH-C(=O)-C$_6$H$_4$-O-CH(CH$_3$)-COO-CH$_2$-CH=CH$_2$ |
| 9. | 2,3-Cl$_2$-C$_6$H$_3$-NH-C(=O)-C$_6$H$_4$-O-CH(CH$_3$)-COO-CH$_2$-C≡CH |

TABLE 1-continued

Compound No.

10. 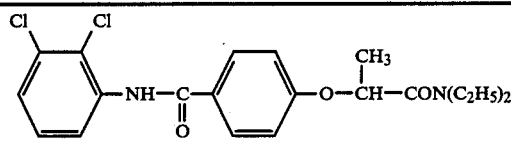

11. 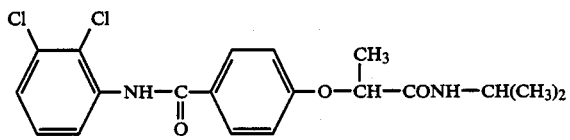

12. 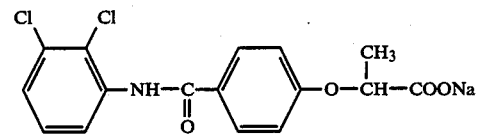

13. 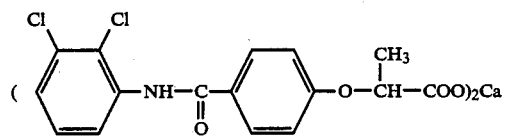

14. 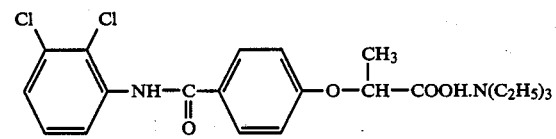

15. 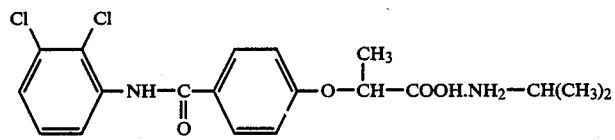

16. (Comparative) 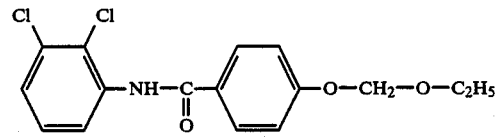

TEST EXAMPLE 1

Foliar treatment tests on various plants (basic)

Rice (*Oryza sativa*), barley (*Hordeum vulgare*), French bean (*Phaseolus vulgaris* L.), tomato, lettuce and slender amarauth (*Amaranthus viridis*) were separately grown in porous pots of 60 cm$^2$, and thinned depending upon the size of the plants. The growth degrees were adjusted to a level of from 2 to 3 leaf stage, and a diluted solution of each regulant was applied in an amount of 10 liter/a. One month later, the growth inhibition was evaluated. The results are shown in Table 2.

The evaluation was made in accordance with the following standards:

0: Same as no treatment
1: Growth inhibition of about 20% as compared with no treatment
2: Growth inhibition of about 40% as compared with no treatment
3: Growth inhibition of about 60% as compared with no treatment
4: Growth inhibition of about 80% as compared with no treatment
5: No progress in growth observed since the treatment
T: Tillering or branching increased remarkably
B: Burning of leaves observed.

TABLE 2

| Compound No. | Concentration (%) | Test plants Response value | | | | | |
|---|---|---|---|---|---|---|---|
| | | RI* | BA* | FR* | TO* | LE* | SL* |
| 1 | 0.03 | 2 | 1 | 3 | 1 | 1 | 4 |
| | 0.1 | 3 T | 2 | 4.5 | 3 | 2 | 5 |
| | 0.3 | 4.5 | 4 T | 5 | 4 | 4 | 5 |
| 2 | 0.03 | 2 | 2 | 4 | 2 | 2 | 4 |
| | 0.1 | 3 T | 3 T | 4.5 | 3 | 3 | 4.5 |
| | 0.3 | 4.5 | 4 | 5 | 4.5 | 4 | 5 B |
| 3 | 0.03 | 2 | 2 | 4 | 2 | 2 | 4 |
| | 0.1 | 3 T | 3 T | 4.5 | 3 | 3 | 4.5 |
| | 0.3 | 4.5 | 4 | 5 | 4 | 4.5 | 5 B |
| 4 | 0.03 | 2 | 2 | 3 | 2 | 2 | 3 |
| | 0.1 | 3 T | 3 T | 4 | 3 | 3 | 4.5 |
| | 0.3 | 4 | 4 | 4.5 | 3 T | 4.5 | 5 |
| 5 | 0.03 | 1 | 2 | 4 | 2 T | 3 | 3 |
| | 0.1 | 2 | 3 T | 4 | 3 T | 4 | 4.5 |
| | 0.3 | 3 T | 4 | 4.5 | 3 | 5 | 5 |
| 6 | 0.03 | 2 | 3 | 3 | 3 T | 3 | 3 |
| | 0.1 | 3 T | 4 | 4 | 3 | 4.5 | 4 |

TABLE 2-continued

| Compound No. | Concentration (%) | Test plants Response value | | | | | |
|---|---|---|---|---|---|---|---|
| | | RI* | BA* | FR* | TO* | LE* | SL* |
| 7 | 0.3 | 4.5 | 4.5 | 5 B | 4 | 5 | 5 B |
| | 0.03 | 2 | 1 | 3 | 2 | 2 | 3 |
| | 0.1 | 2 | 2 | 4 | 3 T | 4 | 4 |
| | 0.3 | 3 T | 3 T | 4.5 | 4 | 4.5 | 5 |
| 8 | 0.03 | 2 | 2 | 3 | 1 | 2 | 4 |
| | 0.1 | 3 T | 3 T | 4 | 3 | 3 | 4.5 |
| | 0.3 | 4 | 4 T | 4.5 | 4 | 4 | 5 |
| 9 | 0.03 | 2 | 2 | 4 | 2 | 2 | 4 |
| | 0.1 | 3 T | 3 T | 4.5 | 3 | 3 | 4.5 |
| | 0.3 | 4 | 4.5 | 5 | 4 | 4 | 5 B |
| 10 | 0.03 | 2 | 1 | 1 | 1 | 1 | 3 |
| | 0.1 | 2 | 2 | 3 | 2 T | 2 | 4 |
| | 0.3 | 3 T | 3 T | 4.5 | 3 T | 2 | 5 |
| 11 | 0.03 | 1 | 1 | 2 | 1 | 1 | 3 |
| | 0.1 | 2 | 2 | 3 | 2 T | 2 | 4 |
| | 0.3 | 3 T | 3 T | 4 | 3 T | 3 | 5 |
| 12 | 0.03 | 3 T | 2 T | 3 | 1 | 1 | 4 |
| | 0.1 | 4 | 3 T | 4 | 2 | 2 | 5 |
| | 0.3 | 4.5 | 4 | 4.5 | 3 | 3 | 5 B |
| 13 | 0.03 | 3 T | 2 T | 2 | 1 | 1 | 3 |
| | 0.1 | 4 | 3 T | 3 | 2 | 2 | 5 |
| | 0.3 | 4 | 3 T | 4 | 3 | 3 | 5 |
| 14 | 0.03 | 3 T | 2 T | 3 | 1 | 2 | 4 |
| | 0.1 | 4 | 3 T | 4 | 3 | 3 | 5 |
| | 0.3 | 4.5 | 4 | 5 | 4 | 4 | 5 B |
| 15 | 0.03 | 3 T | 2 | 4 | 1 | 1 | 4 |
| | 0.1 | 4 | 3 T | 4 | 3 | 3 | 5 |
| | 0.3 | 4.5 | 4 | 5 | 4.5 | 4 | 5 |
| 16 (Comparative) | 0.03 | 0 | 0 | 0 | 0 | 0 | 0 |
| | 0.1 | 0 | 0 | 0 | 0 | 0 | 0 |
| | 0.3 | 0 | 0 | 0 | 0 | 0 | 1 |

*RI: Rice
BA: Barley
FR: French bean
TO: Tomato
LE: Lettuce
SL: Slender amarauth

TEST EXAMPLE 2

Foliar treatment test on paddy field rice

A paddy field to which paddy field rice seedlings (Koshihikari) were transplanted by a transplanter in a usual manner, was divided into unit plots of 6 rows×3 m. Each regulant diluted with water to a predetermined concentration was uniformly sprayed in an amount corresponding to 15 liter/a by a hand sprayer on 25 days and 7 days prior to heading. After the harvest, the stem length and the panicle weight were measured with respect to 20 plants. The moderate lodging was observed at the non-treated plots, and the plots where the lodging reducing effect was distinctly observed was marked with ○. The results are shown in Table 3.

The numerical values represent percentage values relative to the non-treated plots, and the values in the brackets ( ) are the actually measured values.

Further, with respect to the representative plot where the growth inhibition of about 20% was observed, the length between nodes was measured. The results are shown in Table 4.

TABLE 3

| Compound No. | Concentration (ppm) | Treatment on 25 days prior to heading | | | | |
|---|---|---|---|---|---|---|
| | | Stem length (%) | Panicle length (%) | Panicle weight (%) | Lodging reducing effect | Plot No. |
| Foliar treatment test on rice (25 days prior to heading) | | | | | | |
| 1 | 30 | 95 | 106 | 108 | | 1 |
| | 100 | 80 | 100 | 103 | | 2 |
| | 300 | 74 | 102 | 99 | | 3 |
| 3 | 30 | 98 | 105 | 106 | | 4 |
| | 100 | 95 | 103 | 105 | | 5 |
| | 300 | 83 | 98 | 101 | | 6 |
| 7 | 30 | 103 | 101 | 105 | | 7 |
| | 100 | 94 | 104 | 99 | | 8 |
| | 300 | 79 | 102 | 100 | | 9 |
| 10 | 30 | 102 | 100 | 103 | | 10 |
| | 100 | 96 | 101 | 99 | | 11 |
| | 300 | 83 | 99 | 102 | | 12 |
| 12 | 30 | 90 | 103 | 106 | | 13 |
| | 100 | 79 | 104 | 99 | | 14 |
| | 300 | 72 | 99 | 98 | | 15 |
| 14 | 30 | 88 | 100 | 103 | | 16 |
| | 100 | 77 | 105 | 100 | | 17 |
| | 300 | 70 | 98 | 99 | | 18 |
| No treatment | | 100 (79.7 cm) | 100 (18.9 cm) | 100 (3.30 g) | | 19 20 21 |
| Foliar treatment test on rice (7 days prior to heading) | | | | | | |
| 1 | 30 | 99 | 102 | 102 | | 51 |
| | 100 | 85 | 105 | 100 | | 52 |
| | 300 | 74 | 99 | 101 | | 53 |
| 3 | 30 | 100 | 105 | 102 | | 54 |
| | 100 | 92 | 103 | 103 | | 55 |
| | 300 | 87 | 97 | 99 | | 56 |
| 7 | 30 | 101 | 105 | 100 | | 57 |
| | 100 | 87 | 100 | 104 | | 58 |
| | 300 | 79 | 106 | 99 | | 59 |
| 10 | 30 | 99 | 101 | 99 | | 60 |
| | 100 | 101 | 107 | 104 | | 61 |
| | 300 | 89 | 104 | 105 | | 62 |
| 12 | 30 | 92 | 100 | 102 | | 63 |
| | 100 | 81 | 98 | 100 | | 64 |
| | 300 | 76 | 97 | 98 | | 65 |
| 14 | 30 | 94 | 103 | 103 | | 66 |
| | 100 | 82 | 105 | 101 | | 67 |
| | 300 | 76 | 101 | 100 | | 68 |
| No treatment | | 100 (79.7 cm) | 100 (18.9 cm) | 100 (3.30 g) | | 19 20 21 |

TABLE 4

| Plot No.* | Foliar treatment test on rice (length between nodes) | | | | |
|---|---|---|---|---|---|
| | Length between nodes | | | | |
| | n₀ | n₁ | n₂ | n₃ | n₄ |
| 2 | 97 | 72 | 44 | 77 | 99 |
| 12 | 98 | 82 | 40 | 86 | 97 |
| 59 | 95 | 43 | 80 | 81 | 100 |
| 69 | 91 | 46 | 93 | 89 | 97 |
| Non-treated plot | 100 (34.0 cm) | 100 (18.2 cm) | 100 (13.4 cm) | 100 (9.5 cm) | 100 (3.6 cm) |

*Plot No.: Same as Plot No. in Table 3

TEST EXAMPLE 3

Foliar treatment test on wheat

A field of wheat (Norin No. 61) sown in rows in early November, was divided into unit plots of 3 m×4 m. Each compound diluted to a predetermined concentration was sprayed over the entire surface in a unit plot in an amount corresponding to 15 liter/a on 30 days prior to heading i.e. early April and on 7 days prior to heading i.e. late April.

In late June, the stem length, the panicle length and the number of panicle and the grain weight per unit area were examined with respect to 50 stems. The lodging degree was moderate at the non-treated plots, and the plots where the lodging reducing effect was distinctly observed was marked with O. The results are shown in Table 5.

The numerical values represent percentage values relative to the non-treated area, and the values in the brackets ( ) are the actually measured values.

Further, with respect to the representative plot, the length between nodes was examined. The results are shown in Table 6.

quately wet (25 liter/a). Seven days later, they were trimmed, and 2 months later, the evaluation was conducted by the same standards as in Test Example 1. The results are shown in Table 7.

TABLE 5

| Compound No. | Applied concentration (ppm) (15 l/a) | Stem length | Panicle length | Number of panicles per m$^2$ | Grain weight per m$^2$ | Lodging degree | Plot No. |
| --- | --- | --- | --- | --- | --- | --- | --- |
| \multicolumn{8}{Foliar treatment test on wheat (30 days prior to heading)} |
| 1 | 100 | 98 | 102 | 109 | 99 | | 1 |
|  | 300 | 94 | 99 | 110 | 103 | | 2 |
|  | 1000 | 86 | 100 | 102 | 101 | | 3 |
| 3 | 100 | 101 | 102 | 105 | 104 | | 4 |
|  | 300 | 92 | 104 | 106 | 100 | | 5 |
|  | 1000 | 83 | 98 | 100 | 102 | | 6 |
| 6 | 100 | 95 | 103 | 106 | 102 | | 7 |
|  | 300 | 87 | 101 | 107 | 105 | | 8 |
|  | 1000 | 79 | 99 | 101 | 101 | | 9 |
| 12 | 100 | 102 | 104 | 99 | 101 | | 10 |
|  | 300 | 92 | 102 | 108 | 103 | | 11 |
|  | 1000 | 81 | 98 | 104 | 98 | | 12 |
| 14 | 100 | 97 | 103 | 100 | 105 | | 13 |
|  | 300 | 88 | 102 | 103 | 107 | | 14 |
|  | 1000 | 81 | 99 | 98 | 103 | | 15 |
| Non-treatment | — | 100 (94 cm) | 100 (8.4 cm) | 100 (452 m$^2$) | 100 (469 g/m$^2$) | | 16 17 18 |
| \multicolumn{8}{Foliar treatment test on wheat (7 days prior to heading)} |
| 1 | 100 | 102 | 105 | 98 | 104 | | 51 |
|  | 300 | 96 | 102 | 103 | 101 | | 52 |
|  | 1000 | 88 | 101 | 102 | 102 | | 53 |
| 3 | 100 | 100 | 102 | 104 | 106 | | 54 |
|  | 300 | 94 | 99 | 100 | 103 | | 55 |
|  | 1000 | 85 | 101 | 102 | 102 | | 56 |
| 6 | 100 | 95 | 102 | 103 | 103 | | 57 |
|  | 300 | 86 | 105 | 100 | 105 | | 58 |
|  | 1000 | 82 | 104 | 104 | 99 | | 59 |
| 12 | 100 | 101 | 103 | 101 | 103 | | 60 |
|  | 300 | 93 | 101 | 103 | 104 | | 61 |
|  | 1000 | 85 | 99 | 103 | 100 | | 62 |
| 14 | 100 | 98 | 99 | 102 | 102 | | 63 |
|  | 300 | 89 | 101 | 103 | 101 | | 64 |
|  | 1000 | 83 | 98 | 98 | 102 | | 65 |
| Non-treatment | — | 100 (94 cm) | 100 (8.4 cm) | 100 (452 m$^2$) | 100 (469 g/m$^2$) | | 16 17 18 |

TABLE 6

Measurement of length between nodes of wheat

| Plot No.* | n$_0$ | n$_1$ | n$_2$ | n$_3$ | n$_4$ | Stem length |
| --- | --- | --- | --- | --- | --- | --- |
| 3 | 99 | 84 | 79 | 75 | 73 | 86 |
| 9 | 96 | 75 | 63 | 66 | 75 | 79 |
| 59 | 91 | 73 | 81 | 83 | 95 | 82 |
| 64 | 94 | 79 | 91 | 87 | 97 | 89 |
| Non-treated plot | 100 (32.4 cm) | 100 (25.9 cm) | 100 (16.1 cm) | 100 (12.0 cm) | 100 (6.3 cm) | 100 |

*Plot No.: Same as Plot No. in Table 5

TEST EXAMPLE 4

Each compound diluted to a predetermined concentration was applied to azelea (*Rhododendron indicum*) nursery stocks (height: 25–30 cm) grown in a porous pot of 200 cm$^2$ so that the entire nursery stocks were ade-

TABLE 7

| Foliar treatment test on azelea | | | |
| --- | --- | --- | --- |
| Compound No. | Concentration % | Growth inhibition | Other response |
| 1 | 0.1 | 2 | |
|  | 0.3 | 4 | T |
| 2 | 0.1 | 3 | T |
|  | 0.3 | 4.5 | |
| 4 | 0.1 | 3 | T |
|  | 0.3 | 4 | |
| 5 | 0.1 | 2 | |
|  | 0.3 | 4 | |
| 6 | 0.1 | 4 | |
|  | 0.3 | 4.5 | |
| 11 | 0.1 | 2 | |
|  | 0.3 | 3 | T |
| 12 | 0.1 | 3 | T |
|  | 0.3 | 4 | T |
| 15 | 0.1 | 3 | |
|  | 0.3 | 4.5 | |

TEST EXAMPLE 5

Foliar treatment test on trees

To a solution of a wettable powder of Compound No. 1 having a predetermined concentration, a nonionic surfactant was added so that the applied concentration would be 500 ppm, and the mixture was applied to various trees grown in pots of 200 cm² by means of a spray gun in an amount of 10 liter/a when new branches grew to a few cm after branches were trimmed. For spraying, the pot was placed in a box of 40 cm×50 cm, and the mixture was uniformly sprayed in the box.

Three months later, the growth of the new branches were evaluated by the standards of Test Example 1. The results are shown in Table 8.

The height of the each tree at the time of spraying was as follows.

| | |
|---|---|
| Azalea (*Rhododendron indicum*): | 15–20 cm |
| Box tree (*Buxus microphylla*): | 15–20 cm |
| Chinese hawthorn (*Photinia glabra*): | 30–35 cm |
| Abelia (*Abelia serrata*): | 25–30 cm |
| Spindle tree (*Euonymus japonicus*): | 35–40 cm |
| Enkianthus perulatus: | 25–30 cm |
| Pomegranate (*Punica granatum*): | 25–30 cm |
| Camellia (*Camellia japonica*): | 35–40 cm |
| Juniperus chinensis: | 20–25 cm |

TABLE 8

Foliar treatment test on trees

| | Wettable powder of Compound No. 1 Concentration (%) of antive ingredient | | | |
|---|---|---|---|---|
| | 0.05 | 0.1 | 0.2 | 0.4 |
| *Rhododendron indicum* | 2 | 3.5 | 4.5 | 5 |
| *Buxus microphylla* | 1 | 2 | 4 | 4.5 |
| *Photinia glabra* | 1 | 3 | 4.5 | 5 |
| *Abelia serrata* | 1 | 3 | 4.5 | 5 |
| *Euomymus jeponicus* | 2 | 3 | 4.5 | 5 |
| *Enkianthus perulatus* | 3 | 4 | 5 | 5 |
| *Punica granatum* | 2 | 3 | 5 | 5 |
| *Camellia japonica* | 0 | 2 | 4 | 4.5 |
| *Juniperus chinensis* | 0 | 1 | 3.5 | 4.5 |

TEST EXAMPLE 6

Thinning test on apples

Among branches of an apple tree (Fuji) of 24 years old, similar branches were selected, and 20 days after the full bloom, a solution of each compound having a predetermined concentration was sprayed over the entire branches by means of a hand sprayer. Two months later, the fruit-bearing rate and the side to side diameter were examined. The results are shown in Table 9.

TABLE 9

Thinning test on apples

| | | Test results | | | | |
|---|---|---|---|---|---|---|
| Compound No. | Concentration (ppm) | Number of tested fruits | | Fruit bearing rate (%) | | Average fruit diameter Ratio to non-treated branch (%) |
| | | Center fruits | Side fruits | Center fruits | Side fruits | |
| 1 | 10 | 52 | 161 | 86.5 | 12.4 | 108 |
| | 30 | 55 | 172 | 81.8 | 12.8 | 112 |
| | 100 | 51 | 154 | 68.6 | 7.1 | 106 |
| 13 | 10 | 58 | 175 | 89.7 | 17.1 | 105 |
| | 30 | 63 | 182 | 85.7 | 14.8 | 107 |
| | 100 | 55 | 173 | 85.5 | 8.7 | 113 |
| Non-treated branch | — | 51 | 156 | 84.3 | 26.3 | 100 (36.1 mm) |

TEST EXAMPLE 7

Foliar treatment test on Bermuda grass

Bermuda grass (T-328 variety) was divided into plots of 1 m×1 m. Four days after mowing, a diluted solution of each compound was uniformly applied in an amount corresponding to 10 liter/a to each plot by means of a hand sprayer. One week and two weeks after the application, the evaluation was conducted by the same evaluation standards as used in Test Example 1.

The change in the color of leaves was evaluated under the following standards:

| Color of leaves | | |
|---|---|---|
| Browning: | Slight | B-1 |
| | Little | B-2 |
| | Substantial | B-3 |
| Deepening: | Slight | G-1 |
| | Little | G-2 |
| | Substantial | G-3 |

The results are shown in Table 10.

TABLE 10

Results on foliar treatment test on Bermuda grass

| | | 1 week later | | 2 weeks later | |
|---|---|---|---|---|---|
| Compound | g/a | Inhibition | Color of leaves | Inhibition | Color of leaves |
| 1 | 5 | 4.5 | | 4 | |
| | 10 | 5 | | 5 | |
| | 20 | 5 | G-1 | 5 | G-1 |
| 2 | 5 | 4 | | 3 | |
| | 10 | 5 | | 4.5 | |
| | 20 | 5 | | 5 | G-1 |
| 7 | 5 | 4 | | 3.5 | |
| | 10 | 5 | | 4.5 | |
| | 20 | 5 | | 5 | |
| 10 | 5 | 4 | | 3 | |
| | 10 | 5 | | 4.5 | |
| | 20 | 5 | | 5 | |
| 12 | 5 | 4.5 | | 4 | |
| | 10 | 5 | | 5 | |
| | 20 | 5 | B-1 | 5 | |
| 15 | 5 | 5 | | 4 | |
| | 10 | 5 | | 5 | |
| | 20 | 5 | | 5 | |

TEST EXAMPLE 8

Foliar treatment test on soybean

In a green house, soybean (Enrei) was grown in a 200 cm² pot (1 plant/pot). At the beginning of the 3 leaf stage, each compound diluted to a predetermined concentration and having 500 ppm of a nonionic surfactant added, was applied in an amount corresponding to 10 liter/a. The test was conducted with 3 plants per plot. Two months later, the number of pods formed were examined. The results are shown in Table 11. (The numerical value is an average of 3 plants.)

TABLE 11

| Compound No. | Concentration (ppm) | Number of pods/plant |
|---|---|---|
| 1 | 30 | 29.3 |
| | 100 | 35.7 |
| | 300 | 32.3 |
| 4 | 30 | 28.0 |
| | 100 | 31.7 |
| | 300 | 38.3 |
| 12 | 30 | 23.3 |
| | 100 | 34.3 |
| | 300 | 32.0 |

TABLE 11-continued

| Compound No. | Concentration (ppm) | Number of pods/plant |
|---|---|---|
| Non-treated plot | — | 24.7 |

TEST EXAMPLE 9

Inhibition of flower stem development of radish

A field of early maturing radish (Raphanus sativus) sown in spring and grown to immediately before flower stem development (early June) was divided into plots so that each plot contained 6 plants. The wettable powder, emulsifiable concentrate, aqueous solution and liquid formulation were applied in an amount corresponding to 15 liter/a in the respective plots by means of a pressure sprayer, and the dust and micro-granule formulation were applied manually.

One month later, the evaluation was conducted in the same manner as in Test Example 1. The results are shown in Table 12. (The numerical value is an average of 6 plants.)

TABLE 12

Inhibition of flower stem development of radish

| Compound No. | Formulation type and content | | g/a Formulation | Active ingredient | Test results |
|---|---|---|---|---|---|
| 1 | Dust | 2% | 250 | 5 | 3.2 |
| | | | 500 | 10 | 4.2 |
| | | | 1000 | 20 | 4.6 |
| 2 | Micro-granule formulation | 2% | 250 | 5 | 2.6 |
| | | | 500 | 10 | 3.8 |
| | | | 1000 | 20 | 4.5 |
| 6 | Emulsifiable concentrate | 20% | 25 | 5 | 3.9 |
| | | | 50 | 10 | 4.8 |
| | | | 100 | 20 | 5.0 B |
| 10 | Wettable powder | 40% | 12.5 | 5 | 3.1 |
| | | | 25 | 10 | 3.7 |
| | | | 50 | 20 | 4.5 |
| 12 | Aqueous solution | 100% | 5 | 5 | 3.3 |
| | | | 10 | 10 | 4.2 |
| | | | 20 | 20 | 4.7 |
| 14 | Liquid formulation | 20% | 25 | 5 | 3.5 |
| | | | 50 | 10 | 4.5 |
| | | | 100 | 20 | 4.8 |

TEST EXAMPLE 10

Foliar treatment test on sugar cane

A field of sugar cane planted in spring and grown to the initial stage of ripening, was divided into plots so that each plot contained 6 plants, and 20 ml of a solution having a predetermined concentration of an active ingredient and having a surfactant added is applied by a hand sprayer to the base portion of the top leaves of each stem.

Two months later i.e. at the time of harvesting, some heading was observed in the non-treated plot, whereas no heading was observed in each of the treated plots. The plants were harvested and squeezed, and the sugar content of the pressed juice was measured by means of a polarimetric sugar content meter. The results are shown in Table 13.

TABLE 13

Results of measurement of sugar content of sugar cane

| Compound No. | Concentration of active ingredient (%) | Sugar content (%) |
|---|---|---|
| 1 | 0.1 | 12.97 |
| | 0.3 | 13.56 |
| 4 | 0.1 | 12.69 |
| | 0.3 | 13.33 |
| 10 | 0.1 | 11.93 |
| | 0.3 | 12.88 |
| 12 | 0.1 | 13.14 |
| | 0.3 | 14.02 |
| Non-treated plot | — | 10.36 |

TEST EXAMPLE 11

Foliar treatment test on onion

A field of onion (Shonan Gokuwase) transplanted in autumn and grown to May 10 i.e. 10 days prior to harvesting, was divided into plots of 5.4 m$^2$, and a solution having a predetermined concentration of an active ingredient and having a surfactant added was applied to the foliage in an amount corresponding to 10 liter/a.

The height of plants at the time of application was about 50 cm, and lodging was slightly observed.

After harvesting, 50 onions were arranged in one layer without cutting off their leaves and stored in a storage. On Oct. 30, and on Nov. 15, the sprouting rate and the rottening rate were examined. The results are shown in Table 14.

TABLE 14

Results of sprouting rate test on onion

| Compound No. | Applied concentration (%) | October 30 Sprouting rate (%) | Rottening rate (%) | November 15 Sprouting rate (%) | Rottening rate (%) |
|---|---|---|---|---|---|
| 1 | 0.1 | 12 | 2 | 30 | 4 |
| | 0.3 | 0 | 0 | 2 | 4 |
| 3 | 0.1 | 18 | 0 | 42 | 2 |
| | 0.3 | 2 | 2 | 8 | 4 |
| 6 | 0.1 | 10 | 2 | 38 | 4 |
| | 0.3 | 0 | 6 | 4 | 8 |
| 11 | 0.1 | 24 | 2 | 52 | 4 |
| | 0.3 | 8 | 0 | 16 | 2 |
| 12 | 0.1 | 8 | 2 | 28 | 6 |
| | 0.3 | 0 | 2 | 4 | 4 |
| 15 | 0.1 | 14 | 4 | 32 | 4 |
| | 0.3 | 0 | 0 | 6 | 2 |
| Non-treatment | — | 22 | 4 | 54 | 6 |

EXAMPLE 1

Preparation of wettable powder

To 40 parts by weight of Compound No. 10, 52 parts by weight of kaolin clay and 3 parts by weight of white carbon were added, and the mixture was mixed and pulverized by a kneader. Then, 4 parts of a powdery surfactant Sorpol* 5039 (* trade mark, Toho Kagaku K.K.) and 1 part by weight of Rapizol* BB-75 (*trade mark, Nippon Oil and Fats Co., Ltd.) were mixed to obtain a wettable powder containing 40% by weight of Compound No. 10.

EXAMPLE 2

Preparation of emulsifiable concentrate

Twenty parts by weight of Compound No. 6 was dissolved in 42 parts by weight of xylene and 28 parts by weight of cyclohexanone, and 10 parts by weight of Sorpol 800A was added thereto and dissolved under stirring to obtain an emulsifiable concentrate containing 20% by weight of Compound No. 6.

EXAMPLE 3

Preparation of dust

Five parts by weight of a wettable powder containing 40% by weight of Compound No. 1 prepared in the same manner as in Example 1 was thoroughly mixed with 0.3 part by weight of Rapizol BB-75 and 94.7 parts by weight of clay to obtain a dust containing 2% by weight of Compound No. 1.

EXAMPLE 4

Five parts by weight of a wettable powder containing 40% by weight of Compound No. 2 prepared in the same manner as in Example 1 was added to 93 parts by weight of fine particulate zeolite being stirred in a speed kneader, and while the stirring is continued, 2 parts by weight of polyoxyethylene dodecyl ether diluted with water was poured thereto. The mixture was prepared with a small amount of water until no powder was observed, and the mixture was withdrawn and dried under air stream to obtain a micro-granule formulation containing 2% by weight of Compound No. 2.

The plant growth regulant of the present invention is well absorbed particularly from the foliage of plants, and then transferred in the plant body to exhibit its activities preferentially at the portion where the growth is most active. The exhibition of the activities varies depending upon the compound, the concentration, the type of plants or the growing stage of plants. However, it is assumed that the activities are antagonistic against auxin or gibberellin as the plant hormone.

As specific effects, in the case of gramineous plants, the shortening of the length between nodes is observed after the foliar treatment, and in some cases, tillering is facilitated. Further, with respect to broad leaf plants, the plant growth regulant of the present invention is effective to suppress the formation of new buds, to prevent spindly growth or to promote formation of axillary buds or flower buds.

The plant growth regulant of the present invention is a foliar treatment agent, and thus has merits such that it is quickly effective and is not affected by the nature of soil and the little affected by the change of the temperature. Further, it has a wide range of treatment period ranging from one month prior to heading to immediately prior to heading of rice plants, wheat, etc. It is particularly advantageous for the determination of the necessity of the treatment that the growing state can be observed until a later stage. The earlier the treatment, the better the inhibition of the growth between the nodes at a lower portion. However, even by the treatment immediately prior to heading, there will be little adverse effects to the panicles.

With respect to trees, the plant growth regulant of the present invention brings about no change in the color of leaves unless applied in a high concentration, and a sufficient effect is obtainable even by an application at the peripheral portion.

Further, it has another merit that the application time is long from prior to the trimming to the sprouting of new buds after the trimming.

The plant regulant of the present invention is effective against many kinds of trees ranging from broad leaf trees to coniferous trees. For example, in the case of azelea or spindle tree, it is possible to apply a solution with a low concentration at a level of from 0.05 to 0.4% by weight to entire trees so that they are sole wet, or in the case of highly concentrated solution, the application may be at the peripheral portion only. The trimming may preferably be conducted in 3 to 7 days from the application. After the trimming, the application is preferably made at a stage when new branches grow to a few cm. Further, in the case of immediately after the trimming, it is preferred to apply in such a manner that highly concentrated regulant will deposit on the cut portions.

Further, in the cases of flower trees, when the plant growth regulant of the present invention is applied in a relatively low concentration prior to the formation of flower buds, it is possible to increase the number of flower buds.

In the case of the Bermuda grass, since the plant growth regulant of the present invention is a foliar treatment agent, it is little affected by the nature of soil or by the amount of rain, and is effective better at high grass at the time of application, whereby the entire lawn can be made uniform. Further, the inhibition period is fairly long.

In the case of fruit trees, the growth regulant of the present invention is effective even at a low concentration of from 10 to 100 ppm, to selectively eliminating small fruits having a poor growth rate. On the other hand, in the case of soybean, it is effective to increase the number of pods when applied at the initial stage of growth, and may possibly increase the yield. Further, by the treatment at a later stage, it may be useful to prevent overgrowth, which is applicable not only to soybean but also to other plants.

With respect to root crops, it effectively prevents the degradation of the quality of the edible portion by suppressing the flower stem development. Further, it is effective to suppress heading of sugar cane and to increase the sugar content, and thus it is possible to increase the yield.

Furthermore, with respect to egg plants, it is effective to control spindly growth and promote good seedling.

Thus, the plant growth regulant of the present invention is useful for the control of various crop plants.

We claim:

1. A plant growth regulant containing a benzamide derivative of the formula:

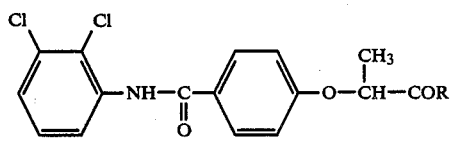

wherein R is hydroxyl, alkoxy, alkoxyalkoxy, alkoxyalkoxyalkoxy, alkenylalkoxy, alkenylalkoxyalkoxy, alkynylalkoxy, alkynylalkoxyalkoxy, monoalkylamino, dialkylamino or O-cat wherein cat is an inorganic or organic cation.

2. The plant growth regulant according to claim 1, wherein the benzamide derivative is selected from the group consisting of

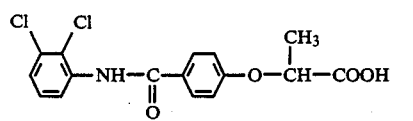
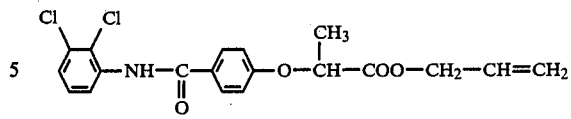
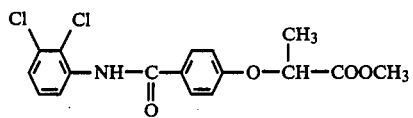
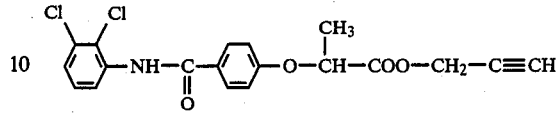
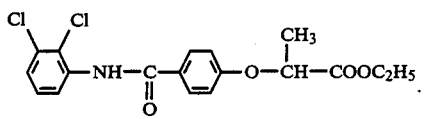
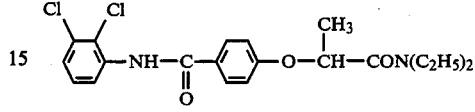
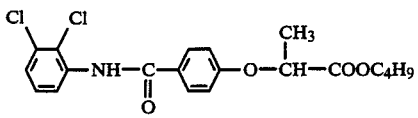
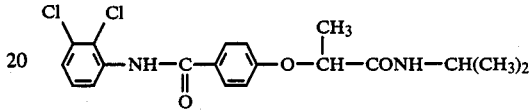
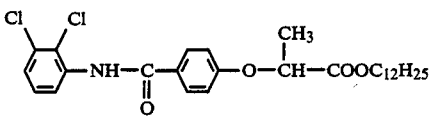
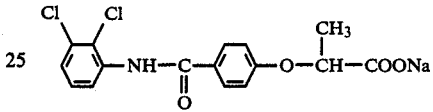
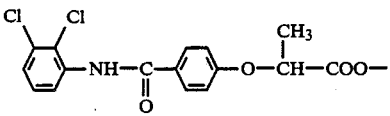
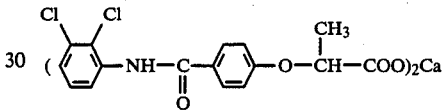
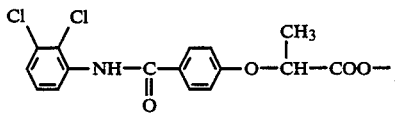
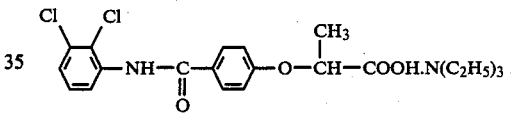
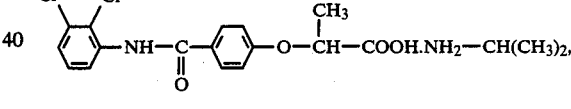
* * * * *